United States Patent [19]

Heinz

[11] Patent Number: 4,643,020
[45] Date of Patent: Feb. 17, 1987

[54] VISCOSIMETER

[76] Inventor: Werner Heinz, Dabringhauserstrasse 72, 5000 Köln-Dellbrück, Fed. Rep. of Germany

[21] Appl. No.: 743,469

[22] Filed: Jun. 11, 1985

[30] Foreign Application Priority Data

Jun. 12, 1984 [DE] Fed. Rep. of Germany ....... 3421715
Jul. 16, 1984 [DE] Fed. Rep. of Germany ....... 3426139

[51] Int. Cl.⁴ .............................................. G01N 11/14
[52] U.S. Cl. ................................................. 73/59
[58] Field of Search ........................... 73/59, 60, 32 R

[56] References Cited

U.S. PATENT DOCUMENTS

| | | | |
|---|---|---|---|
| 2,683,984 | 7/1954 | Boyle et al. | 73/59 |
| 3,113,450 | 12/1963 | Jansson | 73/59 |
| 3,292,422 | 12/1966 | Banks | 73/59 |
| 3,364,730 | 1/1968 | Wall | 73/59 |
| 3,435,666 | 4/1969 | Fann | 73/59 |
| 3,572,086 | 3/1971 | Johnston | 73/59 |
| 3,805,592 | 4/1974 | Miller et al. | 73/32 R |
| 4,148,215 | 4/1979 | Hofstetter, Jr. | 73/59 |
| 4,175,425 | 11/1979 | Brookfield | 73/59 |
| 4,468,953 | 9/1974 | Garritano | 73/59 |
| 4,535,621 | 8/1985 | Gervais et al. | 73/59 |

FOREIGN PATENT DOCUMENTS

| | | |
|---|---|---|
| 1256922 | 7/1968 | Fed. Rep. of Germany . |
| 2258429 | 8/1973 | Fed. Rep. of Germany . |
| 2632076 | 1/1978 | Fed. Rep. of Germany . |
| 3324842 | 1/1984 | Fed. Rep. of Germany . |

Primary Examiner—Michael J. Tokar
Assistant Examiner—Hezron E. Williams
Attorney, Agent, or Firm—David A. Jackson

[57] ABSTRACT

A viscosimeter for measuring the viscous and elastic properties of a visco-elastic substance continuously in or on a process flow comprises a measuring member which extends into the substance and which is displaced with a reciprocating oscillatory movement, whereby a defined constant shear flow occurs between the measuring member and the said substance. The viscosimeter further includes a connecting linkage connecting the measuring member to a drive, the end portion of the connecting linkage which carries the measuring member and which is enclosed by a bellows member being in the form of a carrier member extending normal to the axis of rotational symmetry of the measuring member. The measuring member is connected to the end of the carrier member in such a way that its geometrical axis coincides with the axis of rotational symmetry. The bellows member only performs pure angular movements which give rise to only very slight measuring errors and which enable it to enjoy a long service life.

10 Claims, 2 Drawing Figures

VISCOSIMETER

BACKGROUND OF THE INVENTION

There is often a need as for example in various manufacturing processes to be able to measure viscosity in a continuous mode and with a low level of error, for example to establish the viscous and elastic properties of visco-elastic substances. However, in such a situation problems frequently arise by virtue of the fact that the material to be measured is frequently under an elevated pressure and in many cases is also at elevated temperature. In one form of such a viscosimeter, the device comprises a housing which can be fitted to a space or measuring chamber containing the substance in respect of which viscosity measurements are to be taken, the housing defining an internal chamber and having a connecting rod system which is mounted in the housing and which extends into the measuring chamber. A metal bellows member surrounds the connecting system in the measuring chamber and has one end secured to the outside of the wall of the housing. The viscosimeter further includes a measuring system comprising a rotationally symmetrical measuring member at the end of the connecting system which projects into the measuring chamber, together with a drive means including a torque measuring means operatively connected to the connecting system to produce a measuring flow as between the measuring member and the material in the measuring chamber. It will thus be appreciated that, having regard to the above-mentioned general likelihood of the material to be measured being under elevated pressure and possibly also at elevated temperature, it is necessary for the connecting system to be carefully sealed off with respect to the torque measuring means. As a further consideration in that respect, the sealing means should, as far as possible, not give rise to any force or torque losses, as otherwise that would result in measuring errors.

In one particular design of such a viscosimeter, as disclosed in German patent specification No. 2 632 076, the measuring member rotates continuously and it is only the viscous properties of the material to be measured that it determines. The rotary movement is transmitted in a friction-free manner into the measurement chamber by way of a magnetic coupling means. However, angular displacement may occur as between the two halves of the magnetic coupling means, in dependence on the torque produced. It will be appreciated that it would be difficult accurately to oversee and assess such angular displacement. Furthermore, while such angular displacement is not a major problem in the case of a viscosimeter which operates by virtue of a continuous rotary movement of the measuring member, it is however a problem in the case of an oscillatory viscosimeter of the general kind just discussed above. Thus, in such an oscillatory viscosimeter, there must be a clear association between the angular phase position of the driven measuring member which is disposed in the measuring chamber, and the position of the drive means for driving same. Desirably, the degrees of displacement should be identical under all circumstances.

In another design of viscosimeter, as disclosed in German patent specification No. 2 330 964, the measuring member also rotates continuously, being driven by a hollow shaft which extends into the measuring chamber. The degree of twist of the shaft constitutes a measurement in respect of the torque value involved. However, it will be noted that the hollow shaft which thus serves at the same time as the torque measuring means is exposed to the thermal, chemical and abrasive effects of the material being measured, while in addition the point at which it passes into the measuring chamber must be suitably sealed by means of a gland or like sealing arrangement. That can give rise to serious difficulties, having regard to the above indicated properties of the material to be measured.

Other oscillatory viscosimeters which provide for continuous rotation are also known, as disclosed for example in German patent specification No. 2 006 119 and U.S. Pat. No. 2,683,984 to Boyle et al, wherein the measuring shaft is enclosed by a metal bellows and in that way is sealed off, without however giving rise to a frictional effect. The longitudinal axis of the metal bellows in that arrangement extends approximately parallel to the axis of rotation of the system. However, in those designs, the axis of rotation does not coincide with the geometrical axis of the measuring member so that the measuring member performs a wobble movement as it rotates. As a consequence, the measuring flow which is produced in that way cannot be ascertained mathematically, and the arrangement does not produce defined shear conditions insofar as, with the wobble motion, what is produced is not a straightforward parallel or stratified flow which can be used as a basis for computation, but a displacement flow which evades precise computation.

Another form of oscillatory viscosimeter, as disclosed in German laid-open application (DE-OS) No. 33 24 842, comprises an outer cylinder which performs forced rotary oscillatory movements, and an inner cylinder which is coaxial with respect to the outer cylinder and which is fixed to a hollow shaft or to a torsion tube. The degree of twist of the torsion tube which extends into the material in respect of which a measurement is to be taken is measured, such twist in turn depending on the torque involved in the system. A pump urges the material to be measured through the annular gap or clearance between the inner and outer cylinders. That design of viscosimeter suffers from the disadvantage that either the outer cylinder must have a sealing element which is exposed to the material in respect of which measurements are to be taken, or, if no sealing means is provided, some of the material to be measured is lost. The torsion tube which forms the torque measuring means is also exposed to the effect of the material in respect of which measurements are to be taken, while in addition that viscosimeter can only be used in a secondary flow in by-pass relationship to the actual process flow, and not in the process flow itself.

SUMMARY OF THE INVENTION

An otject of the present invention is to provide an oscillatory viscosimeter which provides a satisfactory seal in relation to the environment in which it operates while at the same time giving rise to a defined steady shear flow.

Another object of the present invention is to provide a viscosimeter which provides a satisfactory seal from its environment, without force or torque losses.

Still another object of the present invention is to provide a viscosimeter which affords a high level of measuring accuracy on a long-term basis.

A further object of the present invention is to provide a viscosimeter which can be satisfactorily used directly in a main body of a substance in respect of which viscosity is to be measured, without the need for branching off a portion thereof for viscosimetric purposes.

Still a further object of the present invention is to provide a viscosimeter which is of a simple, compact and balanced design configuration.

Yet another object of the present invention is to provide a viscosimeter having a viscosity measuring member adapted to perform a pure angular movement thereby to attain a high level of precision.

In accordance with the present invention, these and other objects are achieved by an operational oscillatory viscosimeter comprising a housing which can be fitted on to and connected to a measuring chamber. The housing defines an internal space or chamber therewithin, and disposed within same is a connecting rod or linkage means which extends into the measuring chamber containing the material in respect of which measurements are to be made. The viscosimeter further includes a measuring system comprising a rotationally symmetrical measuring member or body disposed at the end of the connecting means which extends into the measuring chamber, as well as a drive means, including a torque measuring means, on the connecting means, for producing a measuring flow between the measuring member and the material in respect of which measurements are to be taken in the measuring chamber. The end of the connecting means which carries the measuring member is formed as a carrier or support means which extends normal to the axis of rotation of the measuring member, and said end of the connecting means, which forms the measuring member carrier means, is enclosed by a bellows means, for example of metal.

In the system according to the invention, the measuring member performs rotary or oscillatory movements about its own geometrical axis, while the metal bellows member which provides for sealing off the interior of the system with respect to the substance in respect of which measurements are to be taken is only subjected to angular movements. When the measuring member which is of an appropriate configuration performs rotary or oscillatory movements about its own geometrical longitudinal axis, the desired defined steady shear flow is produced in consequence, so that the viscosity of the substance to be measured may be measured in absolute numerical terms. As indicated above, the metal bellows means which provides the sealing effect performs only pure angular and axial movements, in respect of which it has a high level of fatigue strength. The bellows means is not subject to torsional movements which would tend to result in its suffering from a very high rate of wear and consequential early failure. The measuring member carrier means which forms a part or the end portion of the connecting system of the viscosimeter according to the invention, together with the metal bellows means surrounding same, performs reciprocating oscillatory movements, in which the metal bellows means and the carrier means generally do not touch each other. It should also be noted that the connecting means extends on the axis of rotation of the viscosimeter, is disposed in the interior thereof, and performs the oscillatory or rotary movements about its own geometrical axis.

As indicated above, the bellows means may comprise a metal, if such is found to be the appropriate material and configuration in specific circumstances. However, instead of a bellows means comprising metal, it would also be possible to use any other flexible hollow cylinder for the purposes of the invention in this respect. Thus for example, it would be possible to use a concertina-like or bellows-like member consisting of plastic material, if appropriate.

In accordance with an embodiment of the invention, the measuring member is connected to the end of the carrier means which is formed by the end portion of the above-mentioned connecting means of the viscosimeter, in such a way that the geometrical axis of the measuring member coincides with the axis of rotation. That construction ensures that the desired defined steady shear flow can be suitably produced.

Such a viscosimeter may be used for measuring the viscous and elastic properties of visco-elastic substances continuously in or on a process flow. The measuring flow which is produced in the measuring chamber in operation of the viscosimeter may be ascertained mathematically, with the measurements being taken under defined shear conditions. The measurement results are obtained in terms of an absolute measurement system. The measurement result is the complex dynamic viscosity $\eta^*$, which is defined as follows:

$$\eta^* = \eta' - i\, G'/\omega$$

in which $\eta'$ denotes the measured dynamic viscosity, $G'$ denotes the storage modulus of elasticity and $\omega$ denotes the angular frequency $2\pi f$ of the measurement oscillation at a frequency $f$. The measurements are made by means of forced rotary oscillations of at least one measuring member. The torques or forces which occur thereat and which depend on the properties of the visco-elastic substance are measured by a torque measuring means for example in the form of a torsion tube. The measuring member is part of a substantially rotationally symmetrical measuring system. Coaxial cylinder systems or plate-and-cone systems are preferred because of the defined shear conditions which obtain therein.

Another advantageous embodiment of the invention provides that the carrier means is connected to the remainder of the connecting or linkage means by way of an angle means, the angle means comprising a first portion which extends in parallel and eccentric relationship to the axis of rotation and a second portion which connects the first portion to the remainder of the connecting means and which extends normal to the axis of rotation of the system. That arrangement provides that the carrier means which is enclosed by the bellows means or corresponding enclosure member is of a length which approximately corresponds to the diameter of the viscosimeter, thereby providing that the center of rotation of the system is disposed approximately at the mid-length position on the bellows means. Accordingly, the bellows means only performs a simple angular movement about its mid-length position. The above-indicated design configuration of the carrier means provides that the length of the bellows means may also be of optimum magnitude. In consideration of those aspects, the bellows means enjoys a long service life, while in addition the bellows means seals the carrier means in a friction-free manner with respect to the measuring chamber and thus the substance in respect of which measurements are to be taken.

In another advantageous embodiment in accordance with the principles of the present invention, the carrier means is secured to the edge of the measuring member, so that the measuring member does not have any further mounting points which are in the actual material in respect of which measurements are to be taken.

The bellows means is caused to be alternately curved due to the pivotal or reciprocating movements of the carrier means, under the effect of the drive means driving same. Now, the pressure obtaining in the measuring chamber containing the substance to be measured means that the curved bellows means could be subjected to forces which could influence the measuring torque and thus result in errors of measurement. In order at least substantially to prevent that from occurring, the viscosimeter in a preferred embodiment therefore includes means for raising the pressure in the interior of the bellows means to the pressure obtaining on the outside thereof. For that purpose, it is proposed in accordance with the invention that the viscosimeter has a cylindrical housing provided with a piston which is displaceably guided therein; the portion of the housing which is on one side of the piston is towards the measuring chamber while the portion of the housing which is on the other side of the piston is towards the above-mentioned space or chamber defined within the housing, that space or chamber being filled with an inert fluid of low viscosity, for example a silicone oil. Thus, with that configuration, the piston extends into the space or chamber defined within the housing and, by virtue of axial movements thereof, can considerably vary the volume of the fluid-filled chamber. In that way, the pressure obtaining in the measuring chamber is transmitted by way of the piston to the fluid-filled chamber in the housing and therewith also to the interior of the bellows means. As a result, the pressures obtaining on the outside and the inside of the bellows means are the same. It should also be noted that, by virtue of its axial movements, the above-mentioned piston is also able considerably to vary the volume of the internal space in the housing, which is filled with fluid, thereby also taking account of major variations in the volume of the fluid, for example as a result of a rise in temperature thereof. The axial movements of the piston, in fault-free operation of the viscosimeter, are always such that equality of pressure obtains as between the measuring chamber containing the substance in respect of which measurements are to be taken, and the chamber containing the fluid within the housing. Because therefore the interior of the bellows means communicates with the above-mentioned internal chamber in the housing, the bellows means is not subjected to pressure forces.

If the amount of space available at the location at which measurements in respect of the visco-elastic substance are to be taken and at which therefore the viscosimeter is to be positioned is only slight, the invention further provides a design configuration wherein the housing for accommodating the piston may be arranged separately from the actual housing of the viscosimeter. For that purpose, an advantageous embodiment provides that the housing carrying the piston is disposed at a location which is remote from the above-mentioned fluid-filled internal chamber of the viscosimeter, with one portion of the housing carrying the piston being connected to the fluid-filled chamber by way of a conduit, while its portion which is towards the measuring chamber is closed off by a flexible diaphragm. In contrast, if there is adequate structural height at the point of installation of the viscosimeter, the invention provides an embodiment wherein the wall of the fluid-filled chamber forms the housing, the piston is suitably guided therein and projects with its one end portion into the measuring chamber, while an axially movable bellows means extends between the wall of the fluid-filled chamber and the end of the piston which extends into the measuring chamber, whereby the fluid-filled chamber and the measuring chamber are sealed off relative to each other.

In accordance with another advantageous feature of the invention, which can be embodied in both of the viscosimeter design types, namely the type which is used where there is adequate height for the piston-carrying housing to be incorporated directly in the viscosimeter structure, on the one hand, and the type which is used where there is inadequate height for that purpose and thus the piston-carrying housing is disposed at a separate location, the viscosimeter may include a telescopic coupling means in the portion of the connecting means which is disposed in the fluid-filled space or chamber in the housing. The telescopic coupling means thereby compensates for alterations or fluctuations in the length of the system.

In accordance with another advantageous feature of the invention, for the purposes of torque measurement, the torque measuring means is formed by a portion of the connecting or linkage means which is disposed in the above-mentioned fluid-filled space or chamber in the housing, and which is in the form of a torsion tube. Thus, the degree of twist imparted to the torsion tube represents a measurement in respect of the torque being transmitted. As indicated, the torsion tube is disposed in the space in the housing which is filled with inert fluid. The fluid is free of contamination material and is only at a moderate temperature, insofar as the part of the viscosimeter which accommodates the torsion tube is generally disposed in the open air. If high temperatures occur in the substance in respect of which measurements are to be taken, such temperatures have only a slight effect in regard to the part of the viscosimeter which includes the torsion tube, thus further contributing towards a high level of measuring accuracy. The torsion tube itself has a very high level of resistance to twisting, so that angular displacement does not occur between the drive means and the measuring member, or, if such angular displacement does in fact occur, it is only very slight.

Another advantageous embodiment of the viscosimeter in accordance with the principles of the present invention further includes a sealing ring which is disposed in an opening in the housing through which the connecting or linkage means extends outwardly. The sealing ring is acted upon by the fluid in the housing, on the inward side of the sealing ring. Since, as already indicated above, the fluid in the housing is inert and is free from contamination, there is no problem involved in providing a suitable seal at that point. As moreover the torsion tube is disposed between the sealing ring and the carrier means, the friction generated by virtue of the presence of the sealing ring does not affect the measurements made.

The measuring system used in the viscosimeter in accordance with the present invention may be a system comprising cylinders which are disposed in mutually coaxial relationship or a plateball system. A desirable embodiment of the principles of the present invention provides that the measuring system comprises first, second and third cylinders which are disposed one around the other in concentric and spaced relationship, the first and third cylinders constituting the outermost and innermost cylinders of the system, as considered in the radial direction thereof, and being connected together and to the housing of the viscosimeter, while the second cylinder is disposed in the annular gap defined between the first and third cylinders and being secured to the carrier means and thus forming the measuring member. It will be seen therefore that this measuring system has a double gap, namely between the first and second cylinders on the one hand and between the second and third cylinders on the other hand. An important consideration in this respect is that any element of volume of the substance to be measured, which is involved in the measurement operation, must be subjected to the same shear loading, for which purpose the above-mentioned gaps must be suitably narrow. A suitable dimension in that respect is of the order of 1 to 2 millimeters. In order to improve material exchange between the gaps, the cylinders, in an advantageous embodiment, may have communicating openings therein.

Further objects, features and advantages of a viscosimeter in accordance with the principles of the present invention will be apparent from the following description and drawings of a preferred embodiment.

DESCRIPTION OF THE PREFERRED EMBODIMENT

Figure 1:
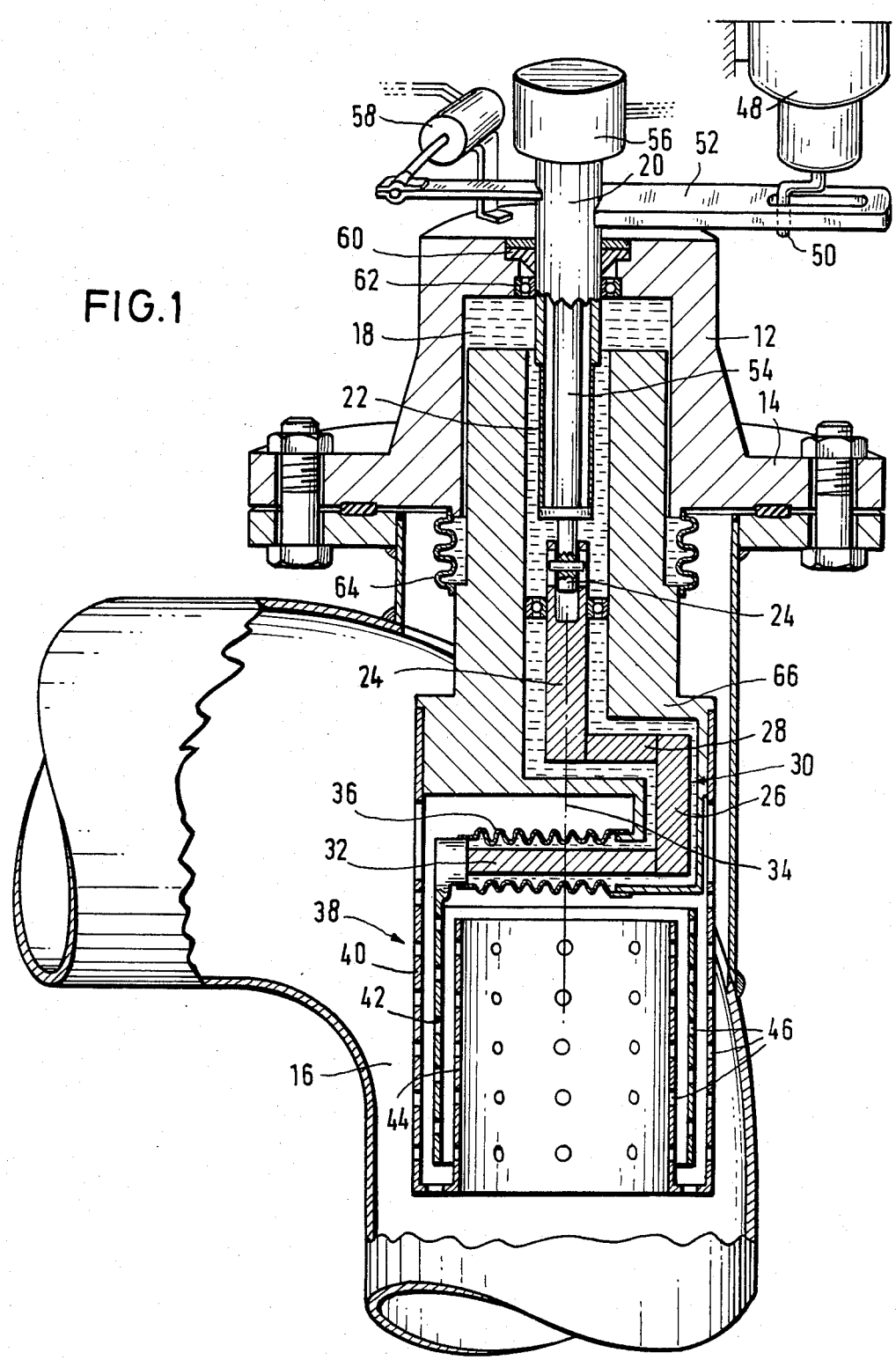
FIG. 1 is a view in longitudinal section of a first embodiment of an operational oscillatory viscosimeter according to the invention.

Referring firstly to FIG. 1, shown therein is a first embodiment of the viscosimeter according to the teachings of the present invention, comprising a housing 12 with a flange 14 having holes (not referenced) for suitably securing the housing to a member containing the substance in respect of which measurements are to be taken, such member therefore defining a measuring chamber. In a practical situation for example the viscosimeter is passed through an opening in for example a conduit or pipeline, and thus pushed into the measuring chamber which is indicated at 16 in FIG. 1.

The housing 12 defines an internal space or chamber which is indicated at 18 and which is filled with an inert fluid. The housing 12 also rotatably mounts an upper shaft portion 20 which extends in the longitudinal direction of the housing 12 from the exterior thereof and through an end wall portion thereof, through the chamber 18. The upper shaft portion 20 is provided for transmitting drive forces for producing a reciprocating movement of the measuring member of the viscosimeter, as will be described in greater detail hereinafter.

Disposed beneath the shaft portion 20 and connected thereto is a torque measuring means in the form of a torsion tube 22. A two-part telescopic coupling means 24 is disposed beneath the torsion tube 22 in FIG. 1, and operatively connected thereto. Joined to the telescopic coupling means 24 is an angle means 30 formed by a first portion 26 which extends vertically in FIG. 1, that is to say, in parallel relationship to the axis of rotation of the upper shaft portion 20, and a second portion 28 which extends at right angles to the portion 26 and thus to the axis of rotation of the shaft portion 20. The portion 28 thus extends horizontally in the view shown in FIG. 1.

Secured to the angle means 30 is a further portion which forms a carrier portion as indicated at 32. The components 20 through 32 can thus be jointly considered as a connecting rod or linkage means for driving the measuring member which will be described hereinafter, with the carrier member 32 thus being formed by the end portion of the connecting means.

As can be clearly seen from FIG. 1, the carrier member 32 extends at an angle of 90° to the longitudinal axis of the viscosimeter, that is to say, the axis of rotation of the connecting means as indicated at 34; the carrier member 32 is of substantially equal length, on respective sides of the axis of rotation 34, in other words, the axis of rotation 34 extends at least substantially through the mid-length position of the carrier member 32.

The carrier member 32 is enclosed by a flexible hollow cylinder member illustrated in the form of a bellows member 36 which comprises for example metal or other suitable material such as a plastic. Disposed beneath the carrier member 32 is the measuring system 38 of the viscosimeter, comprising a first outer cylinder 40, a second cylinder 42 which forms a measuring member of the viscosimeter, and a third cylinder 44 which is disposed radially inwardly of the second cylinder 42. The measuring system thus comprises first, second and third cylinders which are disposed in mutually coaxial relationship. The two cylinders 40 and 44 are connected together and are secured to the housing 12, while the cylinder forming the measuring member 42 is connected to the carrier member 32. It should be noted that the carrier member 32 is connected to the measuring member 42 only by way of the one end portion of the carrier member 32, being more specifically connected to the measuring member 42 at one side thereof.

All the cylinders 40, 42 and 44 have a plurality of openings 46 therein, to provide for interchange of material between the spaces at the various sides of the cylinders.

Still referring to FIG. 1, the viscosimeter includes a d.c. motor 48 having a crank pin 50 which is capable of cooperating with a lever 52 secured to the upper shaft portion 20, thereby to drive the viscosimeter, by producing a reciprocating movement of the connecting means 20 through 32 and therewith the measuring member 42.

The viscosimeter further includes a shaft member 54 which is connected to the torsion tube 22 at the lower end thereof, with the connection being made by way of the upper part of the two-part telescopic coupling 24. The shaft member 54 leads to a travel measuring means which is diagrammatically indicated at 56, forming the torque measuring arrangement.

Reference numeral 60 in FIG. 1 denotes a sealing ring for sealing the interior of the viscosimeter relative to the exterior thereof, at the location at which the upper shaft portion 20 passes through the end wall portion of the housing 12. FIG. 1 also shows a radial ball bearing assembly 62 for rotatably mounting the upper shaft portion 20.

A sealing arrangement illustrated in the form of a bellows 64 is secured to the underneath surface of the flange 14, as viewed in FIG. 1, with the other end of the bellows 64 being connected to a suitable portion of a piston which is indicated generally by reference numeral 66. As can be seen from FIG. 1, the piston is of an inverted generally T-shaped configuration in cross-section, with the upper leg portion of the piston 66 being suitably guided in a space or chamber in the housing 12. The piston 66 is thus displaceable relative to the housing 12, in the direction of the axis of rotation 34 of the system.

Further reference to the purpose of the piston 66 will be set out below.

In operation of the viscosimeter, the motor 48 imparts small reciprocating oscillatory movements to the upper shaft portion 20 and thus to the connecting means 20 through 30 and thus also including the carrier member 32. The oscillatory movements are transmitted to the measuring member 42 of the measuring system 38. Upon such oscillatory movements of the carrier member 32 and the bellows 36 which encloses same, the bellows 36 is retarded in its movements by the substance in respect of which measurements are to be made, in the measuring chamber 16. It should be observed at this point that the end of the bellows 36 which is at the right in FIG. 1 is secured against rotary movement, being welded to a tubular support member. The tubular support member is connected to or formed integrally with the piston 66. Furthermore, the support member virtually coincides with the first portion 26 of the angle means 30, by which the oscillatory movements are transmitted to the measuring system 38. It has been found that only very low levels of interference torques occur. In comparison with the actual measurement torque which is produced in the measuring system 38 by the viscosity of the material in the measuring chamber 16, the resulting measuring error is less than 2%.

As indicated above, the carrier 32 and therewith also the bellows member 36 enclosing same extend at an angle of 90° with respect to the axis of rotation 34, with the carrier member 32 and the bellows member 36 performing oscillatory movements of about ±5° about the axis 34. The bellows 36, in following that movement, is caused to curve towards alternate sides, without however touching the carrier member 32. The center of rotation of the curvature movements of the bellows 36, which coincides with the axis of rotation 34, is at about the mid-length position of the bellows member 36. Thus, the moving end of the bellows member 36, which is at the left in FIG. 1, describes a circular path, with the axis of rotation 34 forming the center point thereof. Thus, the bellows member 36 experiences only pure angular deformation, in only one given direction in each phase of the reciprocating angular movements thereof. As a result, the bellows member is only subjected to a light loading and therefore affords a long service life.

By virtue of the two-part telescopic coupling 24, the carrier member 32 is not directly connected to the upper part of the connecting means, namely the upper shaft portion 20. The measuring system 38, the carrier member 32, the bellows member 36 and the angle means 30 are thus carried by the piston 66 which, as indicated above, is connected to the housing 12 by way of the sealing bellows 64. The space or chamber 18 in the housing 12 is filled with a low-viscosity fluid. As a result of the low viscosity thereof, interference torques which occur due to the oscillating movement of the components in the chamber 18 are only very small and can generally be disregarded. The fluid in the chamber 18 also fills the bellows member 36 and the bellows 64.

In the event of a rise in the pressure in the measuring chamber 66, a force acts on the underside of the piston 16, as viewing in FIG. 1. The piston 66 thus moves upwardly and accordingly seeks to compress the fluid in the chamber 18. Because the fluid in the chamber 18 has a very low degree of compressibility, however, the piston 66 covers only a very short distance before reaching a condition of pressure equilibrium. As a result, the same pressures obtain on the inside and the outside of the bellows member 36, by virtue of the increased pressure applied to the fluid in the chamber 18 by the movement of the piston 66 also being transmitted to the interior of the bellows member 36.

In the event of an increase in the temperature in the measuring chamber 16, the temperature of the fluid in the chamber 18 also rises. Expansion thereof causes a downward movement of the piston 66. The axial movements of the piston 66 which are produced under the above-indicated circumstances are of the order of a few millimeters to about 1 centimeter. The entire measuring assembly follows the axial movements of the piston, without the geometry thereof being fundamentally altered. It will be appreciated that the two-part telescopic coupling means 24 permits such axial movements to take place.

The motor 48, which is controlled in respect of its speed of rotation, produces the oscillatory movement of the measuring system, by way of the crank pin 50 cooperating with the lever 52. The frequency of the oscillatory movements is in a range of from about 0.01 to 10 Hz. The upper shaft portion 20 which forms the input of the connecting system 20 through 32 transmits the oscillatory movements into the housing. In that connection, the frictional losses caused by the sealing ring 60 and the radial ball bearing assembly 62 can be disregarded as the torsion tube 22 which serves for measurement purposes is disposed downstream thereof. The degree of twist imparted to the torsion tube 22 is a measurement in respect of the measuring torque. The twist in the torsion tube is about 0.1° at a maximum, such twist being transmitted to the travel measuring means 56 by way of the shaft member 54. The measuring means 56 may preferably comprise strain gauges. The angular deflection of the rotary oscillatory movement imparted to the system is detected by the inductive displacement pick-up 58. As the connecting system comprising the upper shaft portion 20, the torsion tube 22, the telescopic coupling 24 and the carrier 32 is very resistant to rotational movement within itself, the movement as measured by the pick-up 58 and the movement performed by the measuring member 42 are the same in respect of phase and amplitude. The natural or inherent frequency of that arrangement is about 100 Hz.

The periodic and harmonic torque M as measured by the measuring means 56 and the angle $\theta$ as measured by the pick-up 58 are passed to an electronic evaluation assembly. The evaluation assembly, from M and $\theta$, determines the phase displacement c between the two parameters. From that, it is possible to compute the visco-elastic parameters $\eta'$ and $G'$ of the substance in question, in the following fashion:

$$\eta' = M_o \sin c / \theta_o S \omega; \quad G' = (M_o \cos c + \tau \omega^2 \theta_o)/\theta_o S$$

in which:
$M_o$ = periodic maximum torque
$\theta_o$ = periodic maximum angular deflection
$\tau$ = moment of inertia of all moving parts beneath the torsion tube
$S$ = geometrical resistance factor of the measuring system and
$\omega$ = angular frequency of the oscillation.

Figure 2:
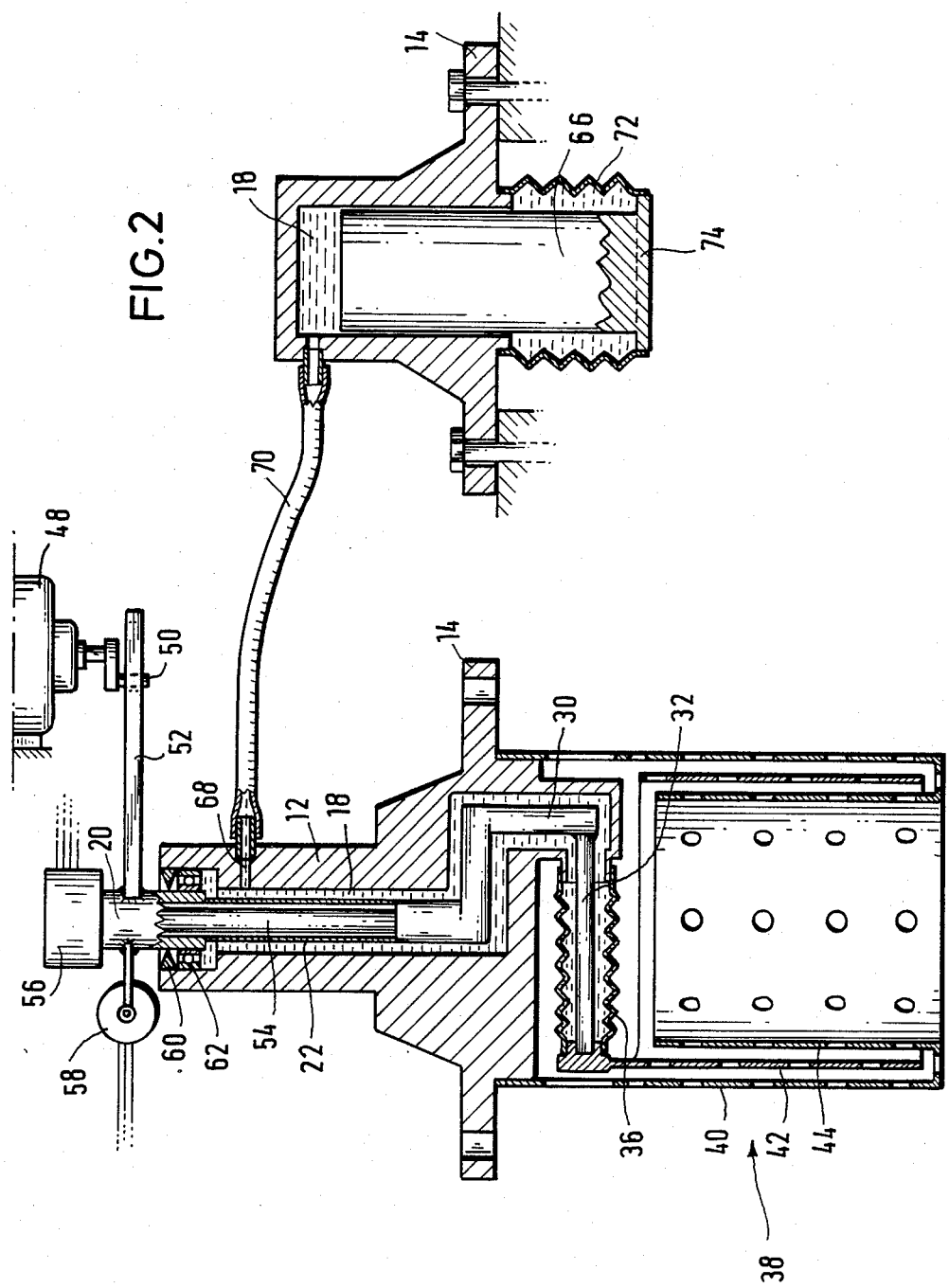
FIG. 2 is a view in longitudinal section through a second embodiment of the viscosimeter wherein a housing which accommodates a compensating piston is arranged at a separate location from the visosimeter housing.

Reference will now be made to FIG. 2 which shows a second embodiment which, as indicated above, is particularly suitable for use in a situation where the available amount of space in terms of height is only slight. Components in the FIG. 2 device which correspond to those of the arrangement described above with reference to FIG. 1 are denoted by the same reference numerals as those used in relation to FIG. 1, and for that reason a detailed description of the FIG. 2 arrangement in its entirety will not be repeated at this point. It will be noted therefore that the piston 66 has been taken out of the actual housing 12 of the device, and is now disposed in a separate housing at a remote location. The separate housing has a flange 14 for fitting it in position, in the same way as the flange 14 on the housing 12 is used for fixing the housing 12 in place. Thus, the further housing which contains the piston 66 may be fitted at another location at an opening in the conduit carrying the flow of substance in respect of which measurements are to be taken. The housing 12 of the actual viscosimeter part of the arrangement has a bore 68 which is communicated by way of a conduit 70 with the chamber 18 in the additional housing which carries the piston 66. The end of the piston 66 which extends downwardly out of the additional housing, as viewing in FIG. 2, is held and sealed off with respect to the material in respect of which measurements are to be taken, by means of a diaphragm or membrane or bellows arrangement, as indicated at 72, and a plate 74.

The arrangement shown in FIG. 2 operates in the same fashion as described above in relation to the FIG. 1 embodiment.

It will be appreciated that the above-described embodiments were set forth only by way of example of the principles of the present invention and that further alterations and modifications may be made therein without departing from the spirit and scope of the invention.

What is claimed is:

1. An oscillatory viscosimeter comprising:
   a housing filled with a liquid and adapted to be connected to a measuring chamber containing a substance having a viscosity to be measured;
   a measuring system including a rotationally symmetrical measuring member having an axis of symmetry, disposed in said measuring chamber when said housing is connected to said measuring chamber;
   oscillatory drive means for producing a rotary movement of said measuring member to thereby produce a measuring flow between said measuring member and said substance in said measuring chamber;
   linkage means rotationally driven in an oscillatory manner, about an axis of rotation in alignment with said axis of symmetry, by said drive means, and extending through said housing, for connecting said drive means to the measuring member, said linkage means including carrier means at an end thereof for carrying said measuring member, said carrier means extending substantially normal to said axis of rotation of said linkage means;
   torque measuring means connected to said linkage means; and
   a flexible hollow metal bellows sealingly enclosing said carrier means.

2. A viscosimeter as set forth in claim 1 wherein said carrier means is connected by way of an angle means to the remainder of said linkage means, said angle means comprising a first portion extending in parallel and eccentric relationship with respect to said axis of rotation and a second portion connecting said first portion to said remainder of said linkage means and extending normal to said axis of rotation.

3. A viscosimeter as set forth in claim 1 wherein said carrier means extends to an extreme outer end of said measuring member.

4. A viscosimeter as set forth in claim 1 wherein a chamber within said housing is filled with a low-viscosity inert fluid, and additionally including a further housing accommodating a piston guided displaceably therein and defining a fluid chamber within said further housing, means communicating said chamber within said housing with the chamber defined in said further housing by said piston, and flexible sealing means sealing said piston to said further housing relative to the exterior thereof.

5. A viscosimeter as set forth in claim 1 further including a piston displaceably guided in said housing and having an end portion adapted to project from said housing into said measuring chamber, and axially movable sealing bellows means extending between said housing and said end portion of the piston which is adapted to project into said measuring chamber for sealing a chamber within said housing and said measuring chamber from each other.

6. A viscosimeter as set forth in claim 1 and including a telescopic coupling means in a portion of said linkage means which is in said chamber within said housing.

7. A viscosimeter as set forth in claim 1 wherein said torque measuring means comprises a portion of said linkage means which is in a chamber within said housing and which is formed as a torsion tube.

8. A viscosimeter as set forth in claim 1 wherein said measuring system comprises first, second and third cylinder members disposed in concentric and spaced relationship, said first and third cylinder members being connected to said housing and said second cylinder member being disposed between said first and third cylinder members and secured to said carrier means, thereby forming said measuring member.

9. A viscosimeter as set forth in claim 8 wherein said cylinder members have openings therethrough.

10. A viscosimeter as set forth in claim 1, wherein said linkage means passes outwardly through an opening in said housing, remote from said measuring chamber, and further including a sealing ring provided in said opening and subjected to pressure from liquid within said housing.

* * * * *